United States Patent
Ferguson et al.

(10) Patent No.: US 11,061,087 B2
(45) Date of Patent: Jul. 13, 2021

(54) DETERMINING A LOAD-OPTIMIZED MR SEQUENCE

(71) Applicant: Siemens Healthcare GmbH, Erlangen (DE)

(72) Inventors: George William Ferguson, Erlangen (DE); Martin Harder, Nuremberg (DE); Daniel Rinck, Forchheim (DE)

(73) Assignee: Siemens Healthcare GmbH, Erlangen (DE)

(*) Notice: Subject to any disclaimer, the term of this patent is extended or adjusted under 35 U.S.C. 154(b) by 41 days.

(21) Appl. No.: 16/516,157

(22) Filed: Jul. 18, 2019

(65) Prior Publication Data
US 2020/0025845 A1 Jan. 23, 2020

(30) Foreign Application Priority Data
Jul. 19, 2018 (DE) .................. 10 2018 212 091

(51) Int. Cl.
| | | |
|---|---|---|
| *G01R 33/28* | (2006.01) | |
| *G01R 33/341* | (2006.01) | |
| *A61B 5/055* | (2006.01) | |
| *G01R 33/34* | (2006.01) | |

(52) U.S. Cl.
CPC ............ *G01R 33/288* (2013.01); *A61B 5/055* (2013.01); *G01R 33/283* (2013.01); *G01R 33/341* (2013.01); *G01R 33/34007* (2013.01)

(58) Field of Classification Search
CPC .. G01R 33/288; G01R 33/341; G01R 33/283; G01R 33/34007; A61B 5/055
See application file for complete search history.

(56) References Cited

U.S. PATENT DOCUMENTS

| | | | |
|---|---|---|---|
| 8,941,380 B2* | 1/2015 | Graesslin ............. | G01R 33/583 324/307 |
| 10,156,621 B2* | 12/2018 | Zhai ..................... | G01R 33/543 |
| 10,682,199 B2* | 6/2020 | Rothgang .............. | A61B 34/20 |
| 2011/0043205 A1* | 2/2011 | Graesslin ........... | G01R 33/5612 324/307 |

(Continued)

FOREIGN PATENT DOCUMENTS

| | | |
|---|---|---|
| DE | 102015203306 A1 | 8/2016 |
| EP | 102016200611 A1 | 7/2017 |

(Continued)

OTHER PUBLICATIONS

German Office Action for German Application No. 10 2018 212 091.9 dated Jun. 11, 2019.

*Primary Examiner* — Dixomara Vargas
(74) *Attorney, Agent, or Firm* — Lempia Summerfield Katz LLC

(57) ABSTRACT

A method includes determining a position of a local coil, a coil position, and a position of a body part of a patient, a body part position. Spacing between the coil position and the body part position is determined. An optimized MR sequence is determined. Based on the determined spacing between the coil position and the body part position, it is checked that in a subsequent MR examination of the patient, a predetermined loading threshold value (e.g., an SAR value) is not exceeded. The optimization of the MR sequence thus takes place under the boundary condition that the loading threshold value is not exceeded.

17 Claims, 2 Drawing Sheets

(56) References Cited

U.S. PATENT DOCUMENTS

| | | | |
|---|---|---|---|
| 2012/0043475 A1* | 2/2012 | Ahn | A61B 6/04 250/453.11 |
| 2013/0053683 A1* | 2/2013 | Hwang | A61B 5/0555 600/413 |
| 2014/0077811 A1* | 3/2014 | Lin | A61B 5/1127 324/309 |
| 2014/0148692 A1* | 5/2014 | Hartmann | A61B 5/062 600/424 |
| 2015/0011865 A1* | 1/2015 | Goldhaber | A61B 5/0035 600/411 |
| 2015/0268321 A1* | 9/2015 | Zhai | G01R 33/583 324/309 |
| 2016/0139217 A1* | 5/2016 | Sakuragi | G01R 33/58 600/415 |
| 2016/0178711 A1* | 6/2016 | Chen | G01R 33/288 324/309 |
| 2017/0042632 A1* | 2/2017 | Rothgang | G01R 33/287 |
| 2017/0205477 A1* | 7/2017 | Grodzki | G01R 33/543 |
| 2017/0205478 A1 | 7/2017 | Brinker | |
| 2017/0248404 A1* | 8/2017 | Freytag | G01R 33/38 |
| 2018/0003791 A1* | 1/2018 | Kimmlingen | G01R 33/563 |
| 2018/0024206 A1 | 1/2018 | Heismann | |
| 2020/0237334 A1* | 7/2020 | Koken | A61B 6/037 |

FOREIGN PATENT DOCUMENTS

| | | |
|---|---|---|
| EP | 102016213579 A1 | 1/2018 |
| EP | 102016214570 A1 | 2/2018 |

\* cited by examiner

DETERMINING A LOAD-OPTIMIZED MR SEQUENCE

This application claims the benefit of DE 10 2018 212 091.9, filed on Jul. 19, 2018, which is hereby incorporated by reference in its entirety.

BACKGROUND

The present embodiments relate to determining an optimized MR sequence.

In medical technology, imaging using magnetic resonance (MR), also referred to as magnetic resonance tomography (MRT) or magnetic resonance imaging (MRI), is distinguished by high soft-tissue contrast levels. When an MR sequence is played out, high frequency excitation pulses (HF pulses) are radiated into an examination object (e.g., a patient), with the result that MR signals are elicited. The MR signals are detected in the MR examination by the magnetic resonance apparatus, for example, with the aid of a local coil. The MR sequence typically also includes gradient pulses in order to provide the MR signals with position encoding. From the detected MR signals, images of the patient may be reconstructed.

The energy of the HF pulses absorbed during the radiating in of the excitation pulses per time unit and per kilogram of body weight is typically designated the specific absorption rate (SAR). The absorption of the HF energy may lead to heating of the body tissue of the patient, so that with an inadmissibly high concentration of HF energy, burning may occur. The energy absorption therefore represents a loading of the patient during an MR examination that may be described by suitable characteristic variables (e.g., the SAR).

SUMMARY AND DESCRIPTION

The scope of the present invention is defined solely by the appended claims and is not affected to any degree by the statements within this summary.

The present embodiments may obviate one or more of the drawbacks or limitations in the related art. For example, an optimized MR sequence without a patient being too severely loaded when the MR sequence is played out is provided. In addition, a highest possible quality of images of the patient and/or a shortest possible examination time may be achieved.

A method for determining an optimized MR sequence having the following acts is provided. A position of a local coil (e.g., a coil position) and a position of a body part of a patient (e.g., a body part position) are determined, and a spacing between the coil position and the body part position is determined. An optimized MR sequence is determined. Based on the determined spacing between the coil position and the body part position, it is checked that in a subsequent MR examination of the patient, a predetermined loading threshold value (e.g., an SAR value) is not exceeded. The optimization of the MR sequence thus takes place under the boundary condition that the loading threshold value is not exceeded.

In one embodiment, an MR examination follows the determination of the optimized MR sequence, whereby the optimized MR sequence is used. The MR examination may include a reconstruction of MR images from the MR signals that have been recorded with the aid of the optimized MR sequence.

The determination of an optimized MR sequence may include, for example, a selection of an MR sequence from existing MR sequences and/or an adaptation of an existing MR sequence. An entirely new MR sequence may, however, also be generated.

The optimized MR sequence may be optimized with regard to a short scan time and/or with regard to a high quality of images that may be generated with the aid of the optimized MR sequence.

One or more of the present embodiments are therefore based, inter alia, upon the recognition that, dependent upon the spacing between the coil position and the body part position, the loading acting upon the patient may be determined particularly easily and effectively. For example, a loading model that is based upon the spacing between the coil position and the body part position may be generated. Based on this loading model, the performance of the subsequent MR examination may be maximized if loading reserves are present or the loading is reduced, if this is necessary.

In one embodiment, the body part position in question is the position of the head of the patient. The position of the head is often particularly important for the loading estimation and thus also for the optimization of the MR sequence. Above all, if the position of the head is not defined by particular circumstances (e.g., if the head is positioned in a head coil that is situated at a defined position of the patient support), the determination of the spacing between the coil position and the body coil position is advantageous. This relates, for example, to examinations in which the patient is introduced feet first into the magnetic resonance apparatus or in which the patient is examined with an arm stretched over the head in the "Superman position." Without a relatively exact loading check, a conservative MR sequence that would possibly take longer and/or would generate only images with relatively low quality may be used.

In one embodiment, the loading threshold includes a local loading threshold for the body part (e.g., the head). If it is assumed that the loading is concentrated during the MR examination above all in the region of the coil position, then typically, the loading falls off with increasing distance from the coil position. In other words, the local loading of the body part at a first spacing between the coil position and the body part position is smaller than at a second spacing between the coil position and the body part position if the first spacing is greater than the second spacing. If the loading threshold value includes a local loading threshold value for the body part, the optimization of the MR sequence may take place more accurately.

In one embodiment, in the subsequent MR examination, the local coil is located in the isocenter of a magnetic resonance apparatus. In the isocenter of the magnetic resonance apparatus, the homogeneity of the magnetic field is particularly high. Therefore, the examination region is typically positioned in order to achieve the best possible image quality. The local coil is usually situated as close as possible to the examination region in order to achieve the greatest possible signal-to-noise ratio (SNR). In the examination region (e.g., where typically the local coil is also positioned) is where the most intense irradiation of the HF pulses typically occurs, so that the potential loading is also greatest there. The further a particularly critical body part (e.g., the head) is removed from the local coil, the lower often is also the loading occurring there. Therefore, the spacing as determined between the coil position and the body part position is particularly suitable for optimizing the MR sequence with regard to the loading.

In one embodiment, the coil position and/or the body part position are determined with an optical detection unit. In one embodiment, the optical detection unit is a camera (e.g., a 3D camera). With this, the body part position may be determined particularly reliably and accurately.

In one embodiment, the optical detection unit detects the body of the patient over a whole length. This facilitates the determination of the position of each body part. Further, the determination of the body part position is then possible regardless thereof in which orientation the patient is placed. For example, the determination of the body part position is possible regardless of whether the patient is situated with the feet or the head first on a patient support of the magnetic resonance apparatus. In one embodiment, the optical detection unit may detect where the body part (e.g., the head) is, the position of which is to be determined, regardless of how the patient is oriented.

In one embodiment, the coil position is determined with a magnetic field sensor (e.g., a Hall-effect sensor). The pattern of the magnetic field in the magnetic resonance apparatus is typically accurately determinable. Together with this information, from the signal of the magnetic field sensor, a position of the magnetic field sensor may be determined accurately and easily. If the relative position of the magnetic field sensor to the local coil is known, the coil position may also be determined easily.

In one embodiment, the magnetic field sensor is arranged on the local coil. For example, the magnetic field sensor may be integrated and/or installed into the local coil. By this, the coil position may be determined easily and accurately.

An embodiment of the method provides that the coil position and the body part position are entered into a coordinate system (e.g., a grid coordinate system). Thereby, the spacing between the coil position and the body part position may be determined particularly easily.

In one embodiment, the subsequent MR examination may be carried out with a magnetic resonance apparatus that has a cylindrical patient receiving region around a longitudinal axis, whereby the spacing between the coil position and the body position is determined along the longitudinal axis. The longitudinal axis may also be designated the z-axis. In such an arrangement, the spacing between the coil position and the body position may represent a particularly useful item of information for optimizing the MR sequence.

Further, a magnetic resonance apparatus is proposed that is configured to carry out a method as described above. The advantages of the proposed magnetic resonance apparatus substantially correspond to the advantages of the method according to one or more of the present embodiments for determining an optimized MR sequence, as described in detail above. Features, advantages, or alternative embodiments mentioned herein may also be transferred to the other subject matter presented here, and vice versa.

In one embodiment, the magnetic resonance apparatus includes a determining unit for determining a coil position and a body part position. The determining unit may include, for example, an optical detection unit for determining the body part position and/or a magnetic field sensor for determining the coil position.

In one embodiment, the magnetic resonance apparatus includes a spacing determining unit for determining a spacing between the coil position and the body part position and an optimizing unit for determining an optimized MR sequence. The spacing determining unit and/or the optimizing unit may include a computer unit that includes, for example, one or more processors.

In one embodiment, the magnetic resonance apparatus includes a cylindrical patient receiving region around a longitudinal axis. With such a magnetic resonance apparatus, the method may be carried out particularly easily and accurately.

Further, a computer program product (e.g., including a non-transitory computer-readable storage medium) that includes (e.g., stores) a program is provided. The computer program product is directly loadable into a memory store of a programmable system control unit of a magnetic resonance apparatus. The program includes, for example, libraries and auxiliary functions in order to carry out a method according to one or more of the present embodiments when the computer program product is executed in the system control unit of the magnetic resonance apparatus. The computer program product may herein include an item of software with a source code that is still to be compiled and linked or is only to be interpreted, or an executable software code (e.g., instructions) that, for execution, is only to be loaded into the system control unit. Using the computer program product, the method according to one or more of the present embodiments may be carried out rapidly, exactly reproducibly, and robustly. The computer program product is configured such that the computer program product may carry out the method acts using the system control unit. The system control unit is to have the respective pre-conditions such as, for example, a corresponding working memory store, a corresponding graphics card, or a corresponding logic unit so that the respective method acts may be carried out efficiently.

The computer program product is stored, for example, on or includes a computer-readable medium (e.g., a non-transitory computer-readable storage medium) or is deposited on a network or server from where the computer program product may be loaded into the processor of a local system control unit that may be directly connected to the magnetic resonance apparatus or may be configured as part of the magnetic resonance apparatus. Control information of the computer program product may be stored on an electronically readable data carrier. The items of control information of the electronically readable data carrier may be configured such that the items of control information carry out a method according to one or more of the present embodiments when the data carrier is used in a system control unit of a magnetic resonance apparatus. Examples of electronically readable data carriers are a DVD, a magnetic tape or a USB stick, on which electronically readable control information (e.g., software) is stored. If this control information is read from the data carrier and stored in a system control unit of the magnetic resonance apparatus, all the embodiments of the above-described methods may be carried out. One or more of the present embodiments may therefore also proceed from the aforementioned computer-readable medium and/or the aforementioned electronically readable data carrier.

BRIEF DESCRIPTION OF THE DRAWINGS

Parts that correspond to one another are provided with the same reference signs in all the drawings.

DETAILED DESCRIPTION

Figure 1:
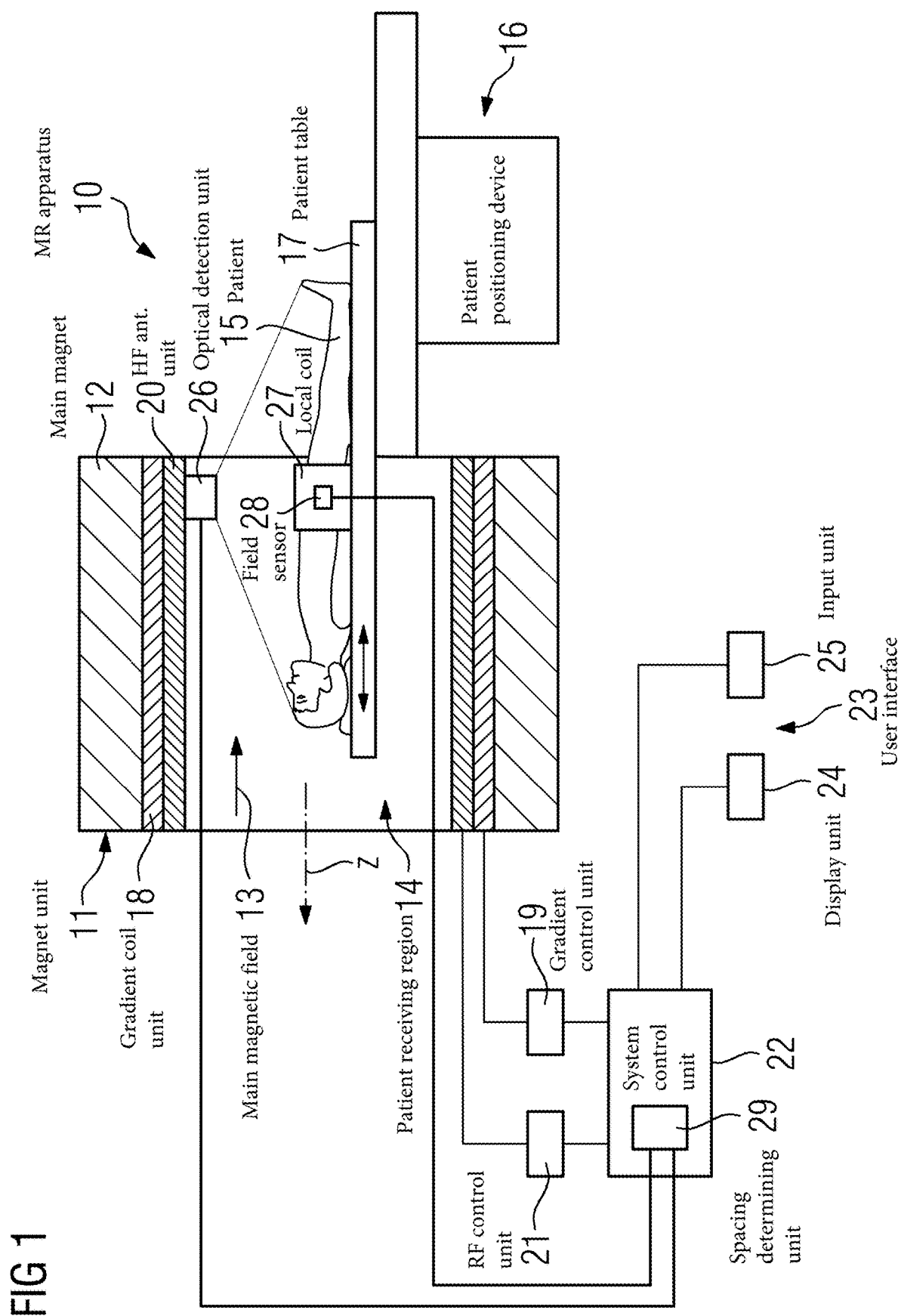
FIG. 1 is a schematic representation of a magnetic resonance apparatus according to an embodiment.

FIG. 1 shows schematically one embodiment of a magnetic resonance apparatus 10. The magnetic resonance apparatus 10 includes a magnet unit 11 that has a main magnet 12 for generating a strong and, for example, temporally constant main magnetic field 13. In addition, the magnetic resonance apparatus 10 includes a patient receiving region 14 to accommodate a patient 15. In the present exemplary embodiment, the patient receiving region 14 is configured as cylindrical about a longitudinal axis z and is surrounded cylindrically in a peripheral direction by the magnet unit 11. A configuration of the patient receiving region 14 deviating therefrom may, however, be provided. The patient 15 may be pushed by a patient positioning device 16 of the magnetic resonance apparatus 10 into the patient receiving region 14. For this purpose, the patient positioning device 16 has a patient table 17 that is configured to be movable within the patient receiving region 14.

The magnet unit 11 also has a gradient coil unit 18 for generating magnetic field gradients that are used for position encoding during an imaging process. The gradient coil unit 18 is controlled by a gradient control unit 19 of the magnetic resonance apparatus 10. The magnet unit 11 further includes a high frequency antenna unit 20 that is configured in the present exemplary embodiment as a body coil that is firmly integrated into the magnetic resonance apparatus 10. The high frequency antenna unit 20 is configured for an excitation of atomic nuclei, which arises in the main magnetic field 13 generated by the main magnet 12. The high frequency antenna unit 20 is controlled by a high frequency antenna control unit 21 of the magnetic resonance apparatus 10 and radiates high frequency MR sequences into an examination space that is substantially formed by a patient receiving region 14 of the magnetic resonance apparatus 10. The high frequency antenna unit 20 is also configured for receiving MR signals.

For controlling the main magnet 12, the gradient control unit 19 and, for controlling the high frequency antenna control unit 21, the magnetic resonance apparatus 10 have a system control unit 22. The system control unit 22 centrally controls the magnetic resonance apparatus 10 (e.g., the execution of a pre-determined imaging gradient echo sequence). Further, the system control unit 22 includes an evaluation unit (not shown in detail) for evaluating medical image data that is acquired during the magnetic resonance examination. Further, the magnetic resonance apparatus 10 includes a user interface 23 that is connected to the system control unit 22. Control information such as, for example, imaging parameters and reconstructed magnetic resonance images may be displayed on a display unit 24 (e.g., on at least one monitor) of the user interface 23 for medical operating personnel. In addition, the user interface 23 has an input unit 25 by which the information and/or parameters may be input by the medical operating personnel during a scanning procedure.

The magnetic resonance apparatus 10 further includes a local coil 27 that is, for example, arranged on the examination region of the patient. Local coils may be receiving coils for the receiving of MR signals. The local coils may, however, also be capable of emitting HF pulses. At the time point of acquiring the MR signals, the examination region and thus also the local coil 27 is located in the isocenter of the magnetic resonance apparatus, which may be situated in the middle of the patient receiving region.

The magnetic resonance apparatus 10 also includes an optical detection unit 26 in the form of a 3D camera (e.g., a camera that is capable of acquiring a three-dimensional image). The 3D camera is mounted at a pre-determined site over the patient positioning device 16 and is capable of detecting the body of the patient 15 over the entire length thereof. For example, the 3D camera may detect the position of the head in all possible patient orientations and pass this information on to a spacing determining unit 29.

In addition, a magnetic field sensor 28 in the form of a Hall-effect sensor is arranged on the local coil 27. The magnetic field sensor 28 supplies information items to the spacing determining unit 29, enabling the determination of the position of the local coil 27.

Figure 2:
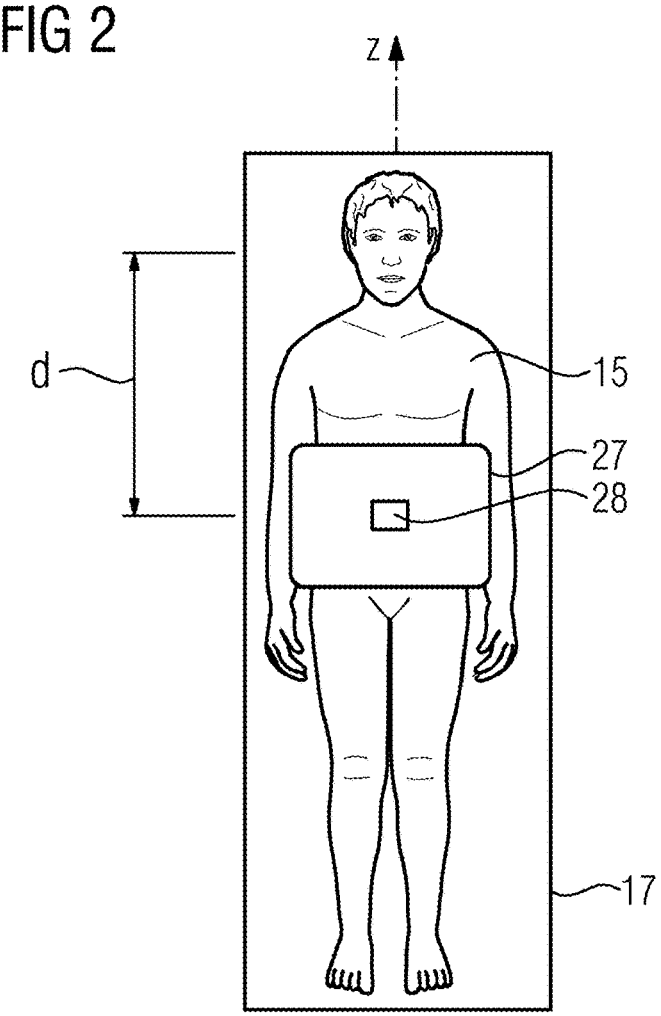
FIG. 2 is a plan view onto a patient.

FIG. 2 shows a plan view onto the patient 15. Also shown is a spacing d between the position of the local coil 27 and the position of the head of the patient.

Figure 3:
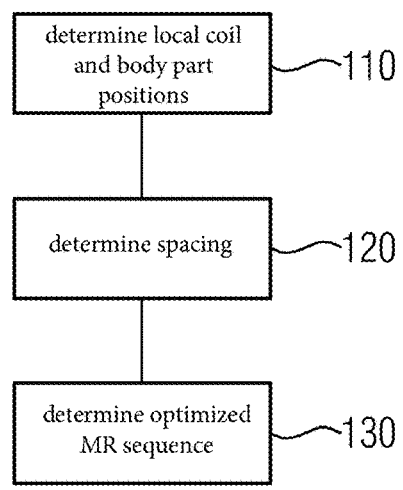
FIG. 3 is a block diagram of one embodiment of a method.

In FIG. 3, one embodiment of a method for determining an optimized MR sequence is shown. In act 110, the position of the local coil (e.g., the coil position) and a position of a body part of a patient (e.g., the body part position) are determined. In act 120, the spacing d between the coil position and the body part position are determined. In act 130, an optimized MR sequence is determined. Thereby, based on the determined spacing between the coil position and the body part position, it is checked that in a subsequent MR examination of the patient, a predetermined loading threshold value is not expected to be exceeded.

The body part in the example shown in FIGS. 1 and 2 is the head of the patient 15. From the position data that the 3D camera 26 and the Hall-effect sensor 28 supply, the spacing determining unit 29 may determine the spacing d between the body part position and the coil position. For example, the spacing may be determined along the longitudinal axis z. For this, the positions may be entered in a grid coordinate system. The grid coordinates may be used to generate a distance-based SAR model that maximizes the performance of the MR examination (e.g., if this is possible in a safe manner) or maximizes the safety (e.g., if this is necessary). This SAR model may include, for example, the dependency that the performance of the MR examination may be increased with a larger distance d.

If, for example, a hip examination is carried out in which the head is introduced first into the patient receiving region 14, this information is typically communicated to the system during the registration. The system then proceeds on the basis, even without the execution of the method of one or more of the present embodiments, that the head of the patient 15 is situated in a defined position, which enables a high-performance SAR model that increases the image quality.

If the same patient is registered for an examination in which the feet are introduced first into the patient receiving region 14, then without the performance of the method of one or more of the present embodiments, a conservative, low-performance SAR model would be selected, since without further information, the position of the head is less accurately known.

According to this exemplary embodiment, the head position and the position of the coils at the hip of the patient 15 are detected. The hip examination may then also be carried out in the same way with high performance, since the spacing from the head is now a known spacing. It is, however, unimportant where the head is situated on the patient table 17.

The method described above in detail and the acquisition template generating unit and the magnetic resonance apparatus disclosed are merely exemplary embodiments that may be modified by a person skilled in the art in a broad variety of ways without departing from the scope of the invention. Further, the use of the indefinite article "a" or "an" does not preclude that the relevant features may also be present plurally. Similarly, the expression "unit" does not preclude the relevant components consisting of a plurality of cooperating subcomponents that may also be spatially distributed if necessary.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining an optimized magnetic resonance (MR) sequence, the method comprising:
   determining a local coil position and a body part position, the local coil position being a position of a local coil and the body part position being a position of a body part of a patient;
   determining a spacing between the local coil position and the body part position;
   determining an optimized MR sequence; and
   checking, based on the determined spacing between the local coil position and the body part position, that in a subsequent MR examination of the patient, a predetermined loading threshold value is not exceeded.

2. The method of claim 1, wherein the predetermined loading threshold value is a specific absorption rate (SAR) value.

3. The method of claim 1, wherein the body part is the head of the patient.

4. The method of claim 1, wherein the loading threshold value comprises a local loading threshold value for the body part.

5. The method of claim 1, wherein the local coil is located in the subsequent MR examination at an isocenter of an MR apparatus.

6. The method of claim 1, wherein determining the local coil position, the body part position, or the local coil position and the body part position comprises determining the local coil position, the body part position, or the local coil position and the body part position with an optical detection unit.

7. The method of claim 6, further comprising detecting, by the optical detection unit, the body of the patient over a whole length.

8. The method of claim 6, wherein the optical detection unit comprises a camera.

9. The method of claim 8, wherein the camera is a three-dimensional (3D) camera.

10. The method of claim 1, wherein determining the local coil position comprises determining the local coil position with a magnetic field sensor.

11. The method of claim 10, wherein the magnetic field sensor comprises a Hall-effect sensor.

12. The method of claim 10, wherein the magnetic field sensor is arranged on the local coil.

13. The method of claim 1, further comprising entering the coil position and the body part position into a coordinate system, in particular, a grid coordinate system.

14. The method of claim 13, wherein the coordinate system is a grid coordinate system.

15. The method of claim 1, further comprising carrying out the subsequent MR examination with a magnetic resonance apparatus that has a cylindrical patient receiving region around a longitudinal axis,
   wherein the spacing between the local coil position and the body position is determined along the longitudinal axis.

16. A magnetic resonance (MR) apparatus for determining an optimized magnetic resonance (MR) sequence, the MR apparatus comprising:
   an optical detection unit or a magnetic field sensor configured to determine a local coil position and a body part position, the local coil position being a position of a local coil and the body part position being a position of a body part of a patient; and
   a processor configured to:
      determine a spacing between the local coil position and the body part position;
      determine an optimized MR sequence; and
      check, based on the determined spacing between the local coil position and the body part position, that in a subsequent MR examination of the patient, a predetermined loading threshold value is not exceeded.

17. In a non-transitory computer-readable storage medium that stores instructions executable by one or more processors to determine an optimized magnetic resonance (MR) sequence, the instructions comprising:
   determining a local coil position and a body part position, the local coil position being a position of a local coil and the body part position being a position of a body part of a patient;
   determining a spacing between the local coil position and the body part position;
   determining an optimized MR sequence; and
   checking, based on the determined spacing between the local coil position and the body part position, that in a subsequent MR examination of the patient, a predetermined loading threshold value is not exceeded.

* * * * *

UNITED STATES PATENT AND TRADEMARK OFFICE
CERTIFICATE OF CORRECTION

PATENT NO. : 11,061,087 B2  
APPLICATION NO. : 16/516157  
DATED : July 13, 2021  
INVENTOR(S) : George Ferguson et al.

Page 1 of 1

It is certified that error appears in the above-identified patent and that said Letters Patent is hereby corrected as shown below:

On the Title Page

(74) Attorney, Agent, or Firm:  
"I.empia Summerfield Katz LLC"

Should be replaced with:  
"Lempia Summerfield Katz LLC"

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*